(12) United States Patent
Gerhardt, Jr. et al.

(10) Patent No.: US 8,840,639 B2
(45) Date of Patent: Sep. 23, 2014

(54) APPARATUS FOR PERFORMING AN ELECTROSURGICAL PROCEDURE

(75) Inventors: Thomas J. Gerhardt, Jr., Littleton, CO (US); Wayne Siebrecht, Golden, CO (US); Keir Hart, Lafayette, CO (US)

(73) Assignee: Covidien LP, Mansfield, MA (US)

( * ) Notice: Subject to any disclaimer, the term of this patent is extended or adjusted under 35 U.S.C. 154(b) by 211 days.

(21) Appl. No.: 12/915,809

(22) Filed: Oct. 29, 2010

(65) Prior Publication Data

US 2012/0109187 A1    May 3, 2012

(51) Int. Cl.
*A61B 17/00* (2006.01)
*A61B 18/14* (2006.01)
*A61B 18/00* (2006.01)
*A61B 17/29* (2006.01)

(52) U.S. Cl.
CPC ..... *A61B 18/1445* (2013.01); *A61B 2018/0091* (2013.01); *A61B 2018/00053* (2013.01); *A61B 2017/2946* (2013.01); *A61B 17/2909* (2013.01)
USPC ........................................................ 606/208

(58) Field of Classification Search
CPC ............... A61B 19/30; A61B 17/2909; A61B 2017/2837; A61B 2017/2845; A61B 2017/2909; A61B 2017/2913; A61B 2017/2915; A61B 2017/2925; A61B 2017/2946
USPC .............................. 606/51, 208, 205–207, 52
See application file for complete search history.

(56) References Cited

U.S. PATENT DOCUMENTS

| D249,549 S | 9/1978 | Pike |
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |

(Continued)

FOREIGN PATENT DOCUMENTS

| DE | 2415263 | 10/1975 |
| DE | 2514501 | 10/1976 |

(Continued)

OTHER PUBLICATIONS

European Search Report for European Application No: 11187266.9 dated Jan. 5, 2012.
U.S. Appl. No. 09/387,883, filed Sep. 1, 1999.
U.S. Appl. No. 09/591,328, filed Jun. 9, 2000.
U.S. Appl. No. 12/336,970, filed Dec. 17, 2008.

(Continued)

*Primary Examiner* — Darwin Erezo
*Assistant Examiner* — Martin T Ton

(57) ABSTRACT

An endoscopic forceps is provided and includes a housing having a handle assembly including a movable handle having a mechanical interface disposed thereon. An end effector assembly connected to a distal end of the shaft includes a pair of first and second jaw members movable relative to one another from an open to a clamping position. A drive assembly includes a resilient member. A lock assembly is pivotably coupled to the housing and in operative communication with the movable handle. The lock assembly is movable with the handle assembly. The mechanical interface moves along the lock assembly when the movable handle is moved proximally causing the lock assembly to rotate about the pivot point and into communication with the resilient member such that the resilient member is prevented from moving distally against the bias provided therefrom such that the first and second jaw members remain in the clamping position.

17 Claims, 11 Drawing Sheets

(56) References Cited

U.S. PATENT DOCUMENTS

| | | | |
|---|---|---|---|
| D348,930 S | 7/1994 | Olson | |
| D349,341 S | 8/1994 | Lichtman et al. | |
| D354,564 S | 1/1995 | Medema | |
| D358,887 S | 5/1995 | Feinberg | |
| 5,413,272 A * | 5/1995 | Green et al. | 227/175.1 |
| 5,425,743 A * | 6/1995 | Nicholas | 606/208 |
| D384,413 S | 9/1997 | Zlock et al. | |
| 5,735,849 A | 4/1998 | Baden et al. | |
| 5,788,710 A | 8/1998 | Bates et al. | |
| 5,792,178 A | 8/1998 | Welch et al. | |
| D402,028 S | 12/1998 | Grimm et al. | |
| 5,957,932 A | 9/1999 | Bates et al. | |
| D416,089 S | 11/1999 | Barton et al. | |
| 5,993,470 A * | 11/1999 | Yoon | 606/185 |
| 6,010,523 A | 1/2000 | Sabin et al. | |
| 6,039,733 A * | 3/2000 | Buysse et al. | 606/40 |
| D424,694 S | 5/2000 | Tetzlaff et al. | |
| D425,201 S | 5/2000 | Tetzlaff et al. | |
| 6,117,158 A | 9/2000 | Measamer et al. | |
| D449,886 S | 10/2001 | Tetzlaff et al. | |
| 6,319,262 B1 | 11/2001 | Bates et al. | |
| D454,951 S | 3/2002 | Bon | |
| D457,958 S | 5/2002 | Dycus et al. | |
| D457,959 S | 5/2002 | Tetzlaff et al. | |
| D465,281 S | 11/2002 | Lang | |
| D466,209 S | 11/2002 | Bon | |
| D493,888 S | 8/2004 | Reschke | |
| D496,997 S | 10/2004 | Dycus et al. | |
| D499,181 S | 11/2004 | Dycus et al. | |
| D502,994 S | 3/2005 | Blake, III | |
| 6,936,052 B2 | 8/2005 | Gellman et al. | |
| D509,297 S | 9/2005 | Wells | |
| 6,991,597 B2 | 1/2006 | Gellman et al. | |
| 7,025,772 B2 | 4/2006 | Gellman et al. | |
| D525,361 S | 7/2006 | Hushka | |
| 7,105,004 B2 * | 9/2006 | Dicesare et al. | 606/170 |
| D531,311 S | 10/2006 | Guerra et al. | |
| D533,274 S | 12/2006 | Visconti et al. | |
| D533,942 S | 12/2006 | Kerr et al. | |
| D535,027 S | 1/2007 | James et al. | |
| D538,932 S | 3/2007 | Malik | |
| D541,418 S | 4/2007 | Schechter et al. | |
| D541,611 S | 5/2007 | Aglassinger | |
| D541,938 S | 5/2007 | Kerr et al | |
| D545,432 S | 6/2007 | Watanabe | |
| 7,235,043 B2 | 6/2007 | Gellman et al. | |
| D547,154 S | 7/2007 | Lee | |
| D564,662 S | 3/2008 | Moses et al. | |
| D567,943 S | 4/2008 | Moses et al. | |
| 7,361,138 B2 | 4/2008 | Wagner et al. | |
| 7,402,133 B2 | 7/2008 | Chu et al. | |
| 7,404,822 B2 | 7/2008 | Viart et al. | |
| D575,395 S | 8/2008 | Hushka | |
| D575,401 S | 8/2008 | Hixson et al. | |
| D582,038 S | 12/2008 | Swoyer et al. | |
| 7,615,066 B2 | 11/2009 | Danitz et al. | |
| 7,628,791 B2 | 12/2009 | Garrison et al. | |
| 7,678,117 B2 | 3/2010 | Hinman et al. | |
| 7,682,307 B2 | 3/2010 | Danitz et al. | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| 7,785,252 B2 | 8/2010 | Danitz et al. | |
| 7,789,878 B2 | 9/2010 | Dumbauld et al. | |
| 7,824,326 B2 | 11/2010 | Wagner et al. | |
| 7,828,808 B2 | 11/2010 | Hinman et al. | |
| 2007/0260242 A1 * | 11/2007 | Dycus et al. | 606/51 |
| 2010/0130977 A1 | 5/2010 | Garrison et al. | |
| 2012/0184988 A1 * | 7/2012 | Twomey et al. | 606/205 |

FOREIGN PATENT DOCUMENTS

| | | |
|---|---|---|
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10045375 | 10/2002 |
| DE | 10 2004 026179 | 12/2005 |
| DE | 20 2007 009317 | 10/2007 |
| DE | 19738457 | 1/2009 |
| EP | 1159926 | 12/2001 |
| EP | 1769767 | 4/2007 |
| JP | 61-501068 | 9/1984 |
| JP | 65-502328 | 3/1992 |
| JP | 5-5106 | 1/1993 |
| JP | 5-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 10-24051 | 1/1998 |
| JP | 11-070124 | 5/1998 |
| JP | 2000-102545 | 9/1998 |
| JP | 11-169381 | 6/1999 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| SU | 401367 | 11/1974 |
| WO | WO 00/36986 | 6/2000 |
| WO | WO 01/54604 | 8/2001 |
| WO | WO 02080799 | 10/2002 |
| WO | WO 2005/110264 | 11/2005 |

OTHER PUBLICATIONS

U.S. Appl. No. 12/429,533, filed Apr. 24, 2009.
U.S. Appl. No. 12/434,382, filed May 1, 2009.
U.S. Appl. No. 12/437,254, filed May 7, 2009.
U.S. Appl. No. 12/503,256, filed Jul. 15, 2009.
U.S. Appl. No. 12/535,869, filed Aug. 5, 2009.
U.S. Appl. No. 12/543,831, filed Aug. 19, 2009.
U.S. Appl. No. 12/548,031, filed Aug. 26, 2009.
U.S. Appl. No. 12/548,534, filed Aug. 27, 2009.
U.S. Appl. No. 12/548,566, filed Aug. 27, 2009.
U.S. Appl. No. 12/551,944, filed Sep. 1, 2009.
U.S. Appl. No. 12/553,509, filed Sep. 3, 2009.
U.S. Appl. No. 12/556,025, filed Sep. 9, 2009.
U.S. Appl. No. 12/556,407, filed Sep. 9, 2009.
U.S. Appl. No. 12/556,427, filed Sep. 9, 2009.
U.S. Appl. No. 12/556,796, filed Sep. 10, 2009.
U.S. Appl. No. 12/562,281, filed Sep. 18, 2009.
U.S. Appl. No. 12/565,281, field Sep. 23, 2009.
U.S. Appl. No. 12/568,199, filed Sep. 28, 2009.
U.S. Appl. No. 12/568,282, filed Sep. 28, 2009.
U.S. Appl. No. 12/568,838, filed Sep. 29, 2009.
U.S. Appl. No. 12/569,395, filed Sep. 29, 2009.
U.S. Appl. No. 12/569,710, filed Sep. 29, 2009.
U.S. Appl. No. 12/574,001, filed Oct. 6, 2009.
U.S. Appl. No. 12/574,292, filed Oct. 6, 2009.
U.S. Appl. No. 12/576,380, filed Oct. 9, 2009.
U.S. Appl. No. 12/597,213, filed Oct. 23, 2009.
U.S. Appl. No. 12/607,191, filed Oct. 28, 2009.
U.S. Appl. No. 12/619,100, filed Nov. 16, 2009.
U.S. Appl. No. 12/692,414, filed Jan. 22, 2010.
U.S. Appl. No. 12/696,592, filed Jan. 29, 2010.

(56) References Cited

OTHER PUBLICATIONS

U.S. Appl. No. 12/696,857, filed Jan. 29, 2010.
U.S. Appl. No. 12/700,856, filed Feb. 5, 2010.
U.S. Appl. No. 12/719,407, filed Mar. 8, 2010.
U.S. Appl. No. 12/728,994, filed Mar. 22, 2010.
U.S. Appl. No. 12/748,028, filed Mar. 26, 2010.
U.S. Appl. No. 12/757,340, filed. Apr. 9, 2010.
U.S. Appl. No. 12/758,524, filed Apr. 12, 2010.
U.S. Appl. No. 12/759,551, filed Apr. 13, 2010.
U.S. Appl. No. 12/769,444, filed Apr. 28, 2010.
U.S. Appl. No. 12/770,369, filed Apr. 29, 2010.
U.S. Appl. No. 12/770,380, filed Apr. 29, 2010.
U.S. Appl. No. 12/770,387, filed Apr. 29, 2010.
U.S. Appl. No. 12/773,526, filed May 4, 2010.
U.S. Appl. No. 12/773,644, filed May 4, 2010.
U.S. Appl. No. 12/775,553, filed May 7, 2010.
U.S. Appl. No. 12/786,589, filed May 25, 2010.
U.S. Appl. No. 12/791,112, filed Jun. 1, 2010.
U.S. Appl. No. 12/792,001, filed Jun. 2, 2010.
U.S. Appl. No. 12/792,008, filed Jun. 2, 2010.
U.S. Appl. No. 12/792,019, filed Jun. 2, 2010.
U.S. Appl. No. 12/792,038, filed Jun. 2, 2010.
U.S. Appl. No. 12/792,051, filed Jun. 2, 2010.
U.S. Appl. No. 12/792,068, filed Jun. 2, 2010.
U.S. Appl. No. 12/792,097, filed Jun. 2, 2010.
U.S. Appl. No. 12/792,262, filed Jun. 2, 2010.
U.S. Appl. No. 12/792,299, filed Jun. 2, 2010.
U.S. Appl. No. 12/792,330, filed Jun. 2, 2010.
U.S. Appl. No. 12/822,024, filed Jun. 23, 2010.
U.S. Appl. No. 12/821,253, filed Jun. 23, 2010.
U.S. Appl. No. 12/832,772, filed Jul. 8, 2010.
U.S. Appl. No. 12/833,270, filed Jul. 9, 2010.
U.S. Appl. No. 12/843,384, filed Jul. 26, 2010.
U.S. Appl. No. 12/845,203, filed Jul. 28, 2010.
U.S. Appl. No. 12/846,602, filed Jul. 29, 2010.
U.S. Appl. No. 12/853,896, filed Aug. 10, 2010.
U.S. Appl. No. 12/859,896, filed Aug. 20, 2010.
U.S. Appl. No. 12/859,985, filed Aug. 20, 2010.
U.S. Appl. No. 12/861,198, filed Aug. 23, 2010.
U.S. Appl. No. 12/861,209, filed Aug. 23, 2010.
U.S. Appl. No. 12/876,662, filed Sep. 7, 2010.
U.S. Appl. No. 12/876,668, filed Sep. 7, 2010.
U.S. Appl. No. 12/876,680, filed Sep. 7, 2010.
U.S. Appl. No. 12/876,705, filed Sep. 7, 2010.
U.S. Appl. No. 12/876,731, filed Sep. 7, 2010.
U.S. Appl. No. 12/877,199, filed Sep. 8, 2010.
U.S. Appl. No. 12/877,482, filed Sep. 8, 2010.
U.S. Appl. No. 12/879,505, filed Sep. 10, 2010.
U.S. Appl. No. 12/882,304, filed Sep. 15, 2010.
U.S. Appl. No. 12/895,020, filed Sep. 30, 2010.
U.S. Appl. No. 12/896,100, filed Oct. 1, 2010.
U.S. Appl. No. 12/897,346, filed Oct. 4, 2010.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967, British Medical Journal Feb. 6, 1976, Vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.

(56) References Cited

OTHER PUBLICATIONS

Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. " Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended- EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report Ep 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 157500.9 dated Jul. 30, 2010.
Int'l Search Report EP 10 159205.3 dated Jul. 7, 2010.
Int'l Search Report EP 10 160870,1 dated Aug. 9, 2010.
Int'l Search Report EP 10 161596.1 dated Jul. 28, 2010.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18676 dated Sep. 19, 2003.
Int'l Search Report PCT/US03/28534 dated Dec. 19, 2003.
Int'l Search Report PCT/USO4/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.

* cited by examiner

APPARATUS FOR PERFORMING AN ELECTROSURGICAL PROCEDURE

BACKGROUND

1. Technical Field

The present disclosure relates to an electrosurgical forceps. More particularly, the present disclosure relates to a lock assembly for use with a variety of endoscopic electrosurgical forceps for sealing and/or cutting various tissue structures.

2. Description of Related Art

Electrosurgical instruments, e.g., electrosurgical forceps (closed type), are well known in the medical arts and typically include a housing, a handle assembly including a movable handle, a shaft and an end effector assembly attached to a distal end of the shaft. The end effector includes jaw members configured to manipulate tissue (e.g., grasp and seal tissue). Typically, the electrosurgical forceps utilizes both mechanical clamping action and electrical energy to effect hemostasis by heating the tissue and blood vessels to coagulate, cauterize, seal, cut, desiccate, and/or fulgurate tissue. Usually, one or more driving mechanisms, e.g., a drive assembly including a drive element, is utilized to cooperate with one or more components operatively associated with the handle assembly to impart movement to one or both of the jaw members. To facilitate clamping the jaw members onto tissue, one or more clamping springs (or other suitable device(s)) may be operably associated with the handle assembly, end effector and/or the driving mechanisms.

In certain instances, the movable handle may be configured to lock, via the clamping spring, the jaw members in a clamping position onto tissue disposed therebetween. This type of locking method, i.e., locking the movable handle in the closed position, transfers a portion of the locking force from the compressed clamping spring through the movable handle and to its locking point, i.e., the jaw members. Over time, however, what is typically referred to in the art as handle or lever "flex" changes the compression force of the clamping spring and, thus, reduces or greatly diminishes jaw clamping forces on tissue. In the instance where the jaw members are configured to grasp, clamp and, subsequently, seal tissue, this reduced clamping force on tissue provided by the jaw members may result in a non-uniform and/or ineffective tissue seal, which, in turn, may be deleterious to a patient.

SUMMARY

The present disclosure provides an endoscopic forceps. The endoscopic forceps includes a housing having a shaft that extends therefrom and defines a longitudinal axis therethrough. A handle assembly includes a movable handle movable relative to the housing. The movable handle includes one or more mechanical interfaces disposed thereon. An end effector assembly operatively connects to a distal end of the shaft and includes a pair of first and second jaw members pivotably coupled to one another. One (or in some instances both) of the first and second jaw members is movable relative to the other from an open or neutral position, wherein the first and second jaw members are disposed in spaced relation relative to one another, to a clamping position, wherein the first and second jaw members cooperate to grasp tissue therebetween. A drive assembly includes a resilient member operably associated therewith. A lock assembly operably couples to the housing about a pivot point, and is in operative communication with the movable handle via one or more mechanical interfaces disposed thereon. The lock assembly is movable with the handle assembly. The one or more mechanical interfaces moves along the lock assembly when the movable handle is moved proximally causing the lock assembly to rotate about the pivot point and into communication with the resilient member such that the resilient member is prevented from moving distally against the bias provided therefrom such that the first and second jaw members remain in the clamping position.

The present disclosure provides electrosurgical forceps. The electrosurgical forceps includes a housing having a shaft with a distal end thereof having an end effector assembly operatively connected thereto. The end effector includes a pair of first and second jaw members pivotably coupled and movable relative to one another from an open or neutral position to a clamping position. A movable handle is movable relative to the housing and includes one or more mechanical interfaces disposed thereon. A drive assembly includes a resilient member operably associated therewith. A lock assembly operably couples to the housing about a pivot point and is in operative communication with the movable handle via the one or more mechanical interfaces disposed thereon. The one or more mechanical interfaces moves along the lock assembly when the movable handle is moved proximally causing the lock assembly to rotate about the pivot point and into communication with the resilient member such that the resilient member is prevented from moving distally against the bias provided therefrom such that the first and second jaw members remain in the clamping position.

The present disclosure also provides a lock assembly for use with a surgical instrument. The lock assembly includes a state changing feature having a beam spring at one end thereof and a locking member at an opposite end thereof. The locking member includes a generally arcuate configuration. The state changing feature includes a generally arcuate proximal end. The beam spring is selectively engageable with a housing of the surgical instrument and is configured to rotate the lock assembly in a clockwise and counterclockwise direction and into and out of communication with the housing upon actuation of the lock assembly.

BRIEF DESCRIPTION OF THE DRAWING

Various embodiments of the present disclosure are described hereinbelow with references to the drawings, wherein.

DETAILED DESCRIPTION

Figure 1A:
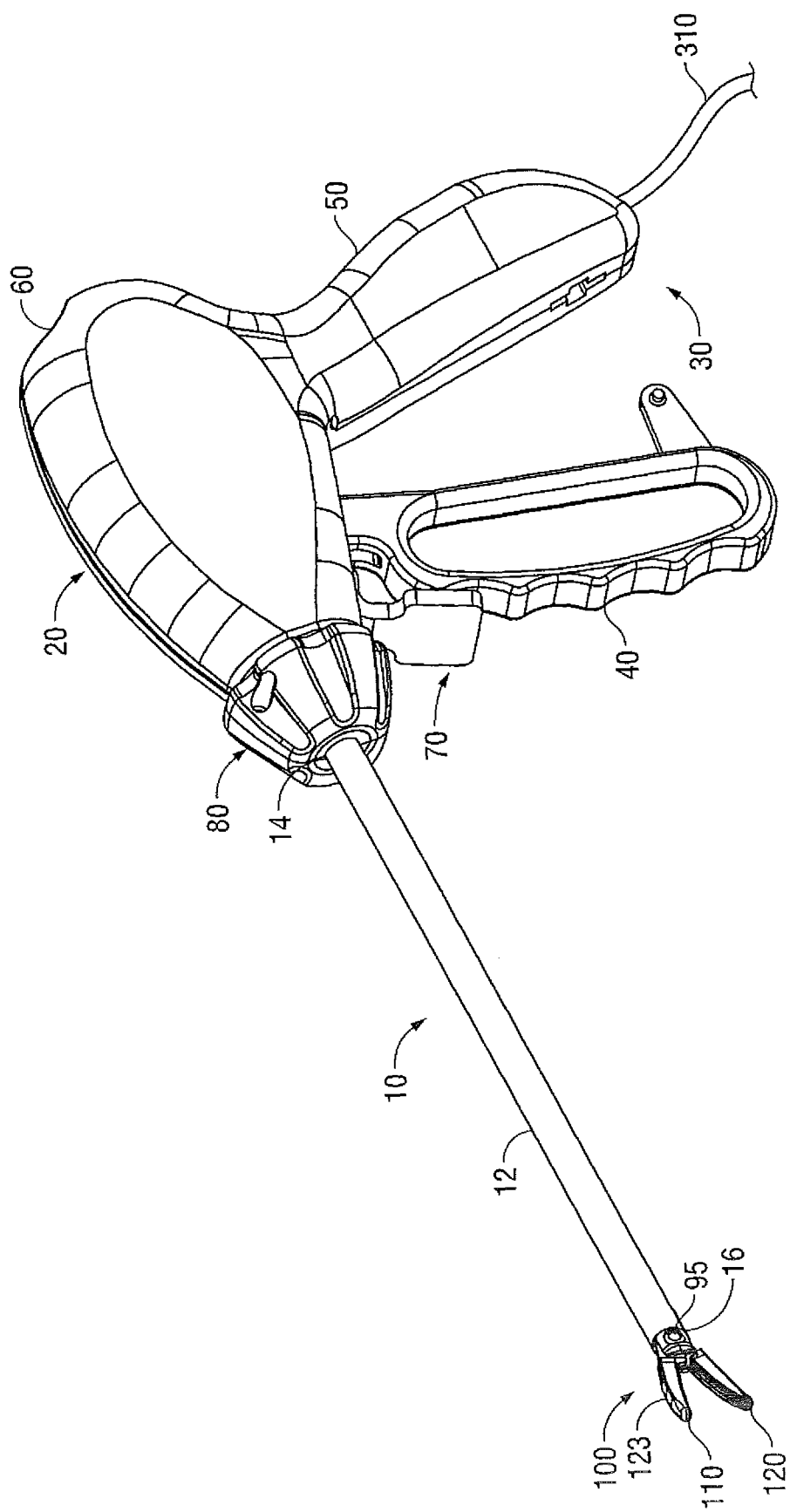
FIG. 1A is a perspective view of a bipolar forceps shown in open configuration and including a housing, a shaft, handle assembly, a lock assembly, trigger assembly and an end effector assembly according to the present disclosure.

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In the drawings and in the descriptions that follow, the term "proximal," as is traditional, will refer to an end which is closer to the user, while the term "distal" will refer to an end that is farther from the user.

Figure 1B:
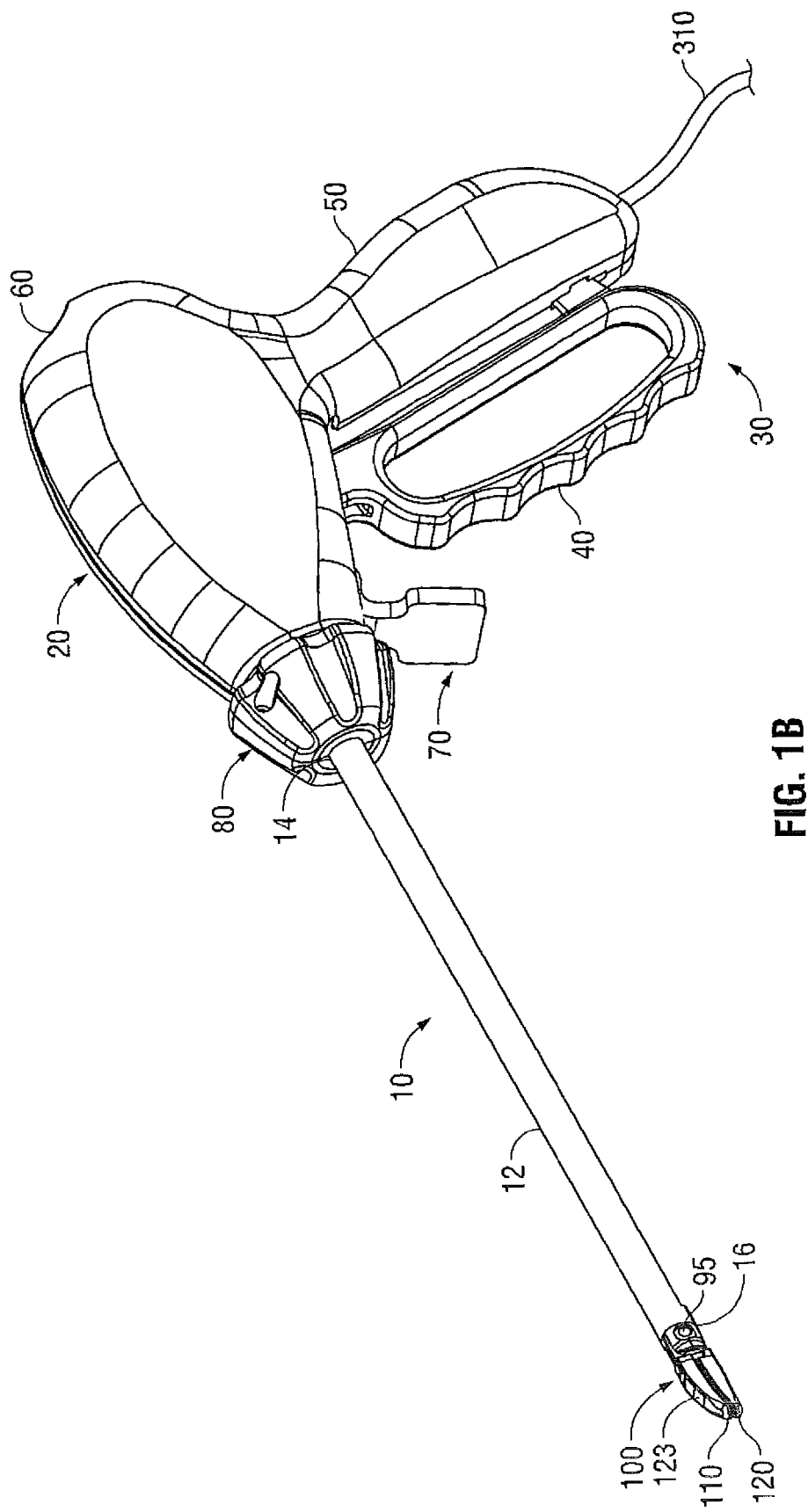
FIG. 1B is a perspective view of the bipolar forceps of FIG. 1A shown in closed configuration.

FIGS. 1A and 1B show in detail the operating features and inter-cooperating components of an endoscopic bipolar forceps for use with the present disclosure generally identified as forceps 10. Briefly, forceps 10 is for use with various surgical procedures and includes: a housing 20; a rotating assembly 80; a trigger assembly 70; a switch 60; an electrosurgical cable 310 for connecting the forceps 10 to an electrosurgical generator (not shown); and an end effector assembly 100. These various components mutually cooperate to grasp, seal and divide tubular vessels and vascular tissues.

With continued reference to FIGS. 1A and 1B, forceps 10 includes a shaft 12 that has a distal end 16 configured to mechanically engage the end effector assembly 100 operably associated with the forceps 10 and a proximal end 14 that mechanically engages the housing 20.

With reference to FIGS. 2A-2D, drive assembly 130 is illustrated. Drive assembly 130 includes a reciprocating drive sleeve 134 slidingly disposed within the shaft 12 that is remotely operable by the drive assembly 130. Specifically, proximal movement of the drive assembly 130 via actuation of handle assembly 30 causes the drive sleeve 134 to reciprocate proximally. The jaw members 110 and 120, in turn, pivot about a pivot pin 95 disposed through respective pivot holes disposed within flanges 113 and 123, as best seen in FIG. 1A.

One or more resilient members (e.g., springs not explicitly shown) are operably associated with drive assembly 130 and are configured to bias the drive assembly including the drive sleeve 134 distally such that the jaw members 110 and 120 are disposed in a normally open or neutral position. More particularly, a spring cartridge 133 is operably disposed in the housing 20 and houses and/or supports one or more suitable springs (not explicitly shown) therein. Spring cartridge 133 is configured (in conjunction with a movable handle 40) to hold or maintain one or both of the jaw members 110 and 120 in a closed or clamping position when the movable handle 40 is moved to a locked position, described in greater detail below.

Handle assembly 30 includes a fixed handle 50 and movable handle 40 (FIGS. 1A-2D). In one particular embodiment, fixed handle 50 is integrally associated with housing 20. Movable handle 40 of handle assembly 30 is ultimately connected to drive assembly 130 (see FIG. 2A, for example) to impart movement of the jaw members 110 and 120 from the open position (FIG. 1A) wherein the jaw members 110 and 120 are disposed in spaced relation relative to one another, to a clamping or closed position (FIG. 1B) wherein the jaw members 110 and 120 cooperate to grasp tissue therebetween.

As best seen in FIGS. 2A-2D, movable handle 40 is selectively movable about a pivot pin 45 from a first position relative to fixed handle 50 to a second position in closer proximity to the fixed handle 50 that imparts movement of the jaw members 110 and 120 relative to one another. As explained in more detail below, continued proximal movement of the movable handle 40 places the movable handle 40 in a locked position, wherein the jaw members 110 and 120 are maintained in the clamping position. To release or "unlock" the movable handle 40 from the locked position, the movable handle 40 is moved proximally past the locked position through a release stroke such that the lock feature 91 releases the spring cartridge and allows movable handle 40 is allowed to move freely, i.e., distally, toward the distal position and the jaw members 110 and 120 return to the open position.

Continuing with reference to FIGS. 2A-2D, the movable handle 40 includes a clevis 46 that forms a pair of flanges (only a right upper flange 46a is described herein). Unless otherwise stated, it is to be understood that the left upper flange includes the same components and is configured to function similar to that of right upper flange 46a. Right upper flange 46a has an aperture (not explicitly shown) at an upper end thereof for receiving pivot 45 therethrough and mounting the upper end of the handle 40 to the housing 20. Upper flange 46a includes a drive flange 47a that is aligned along longitudinal axis "A-A" (see FIG. 1A) and which abuts the drive assembly 130 such that pivotal movement of the handle 40 forces the drive flange 47a against the bias of the spring disposed in the spring cartridge 133, which, in turn, closes and tensions the jaw members 110 and 120 (see FIGS. 1A-2D).

Movable handle 40 provides a distinct mechanical advantage over conventional handle assemblies due to the unique position of the pivot pin 45 relative to the longitudinal axis "A-A" of the shaft 12 and the disposition of the drive flange 47a (and a drive flange associated with the upper left flange) along longitudinal axis "A-A". In other words, by positioning the pivot pin 45 above the driving flange 47a, a user gains a mechanical advantage to actuate the jaw members 110 and 120 enabling the user to close the jaw members 110 and 120 with less force while still generating the required forces necessary to affect a proper and effective tissue seal.

One or more mechanical interfaces, e.g., nubs, protrusions, pins or the like, are operably disposed on the movable handle 40. More particularly, a pin 48 (see, FIG. 2A) of suitable proportion is operably disposed on either (or in certain instances both) sides of the movable handle 40 and on a portion of the movable handle 40 that is configured to move within the confines of the housing 20. For illustrative purposes, pin 48 is shown operably disposed on an interior right side of the movable handle 40. Specifically, the pin 48 is configured to move along a cartridge lock assembly 90 (lock assembly 90) when the movable handle 40 is moved proximally, described in greater detail below. Pin 48 operably couples to lock assembly 90 to pivotally move the lock assembly 90 into a lock position thereby blocking the spring cartridge 133 and for limiting distal movement of the drive assembly 130 including spring cartridge 133 and drive sleeve 134 when the movable handle 40 is moved proximally past a predetermined position and to a locked position.

With reference again to FIGS. 2A-2D, and with reference to FIGS. 3-7, lock assembly 90 is illustrated. Lock assembly 90 may be made from any suitable material including but not limited to plastic, metal, metal alloy, etc. In the illustrated embodiment, lock assembly 90 is made from plastic and is of unitary construction. Alternatively, the components that make up the lock assembly 90 may be joined or coupled together by one or more suitable coupling methods, e.g., adhesive.

Lock assembly 90 pivotably couples to the housing 20 about a pivot point. Specifically, one or more suitable pivot devices and/or mechanisms pivotably couples the lock assembly 90 to the housing 20. More specifically, a pivot pin 94 includes a generally elongated configuration having a pair of lateral edges 94a that extend laterally across the lock assembly 90, see FIGS. 3-5. The pair of lateral edges 94a operably couples the pivot pin 94 to an internal frame of the housing 20 such that the pivot pin 94 pivots thereabout. In the illustrated embodiment, the pair of lateral edges 94a are configured to rotatably reside in a pair of corresponding cavities or bores 20a (shown in phantom in FIGS. 2A-2D) operably disposed on the internal frame of the housing 20.

Proximal movement of the movable handle 40 moves the pin 48 along the lock assembly 90. The lock assembly 90, in turn, rotates about the pivot pin 94 and contacts, i.e., blocks, the spring cartridge 133 such that the spring cartridge 133 is prevented from moving distally against the bias provided therefrom, which, in turn, maintains the movable handle 40 in the locked position and the jaw members 110 and 120 in the clamping position (see FIG. 1B in combination with FIGS. 2A and 2C).

Figure 3:
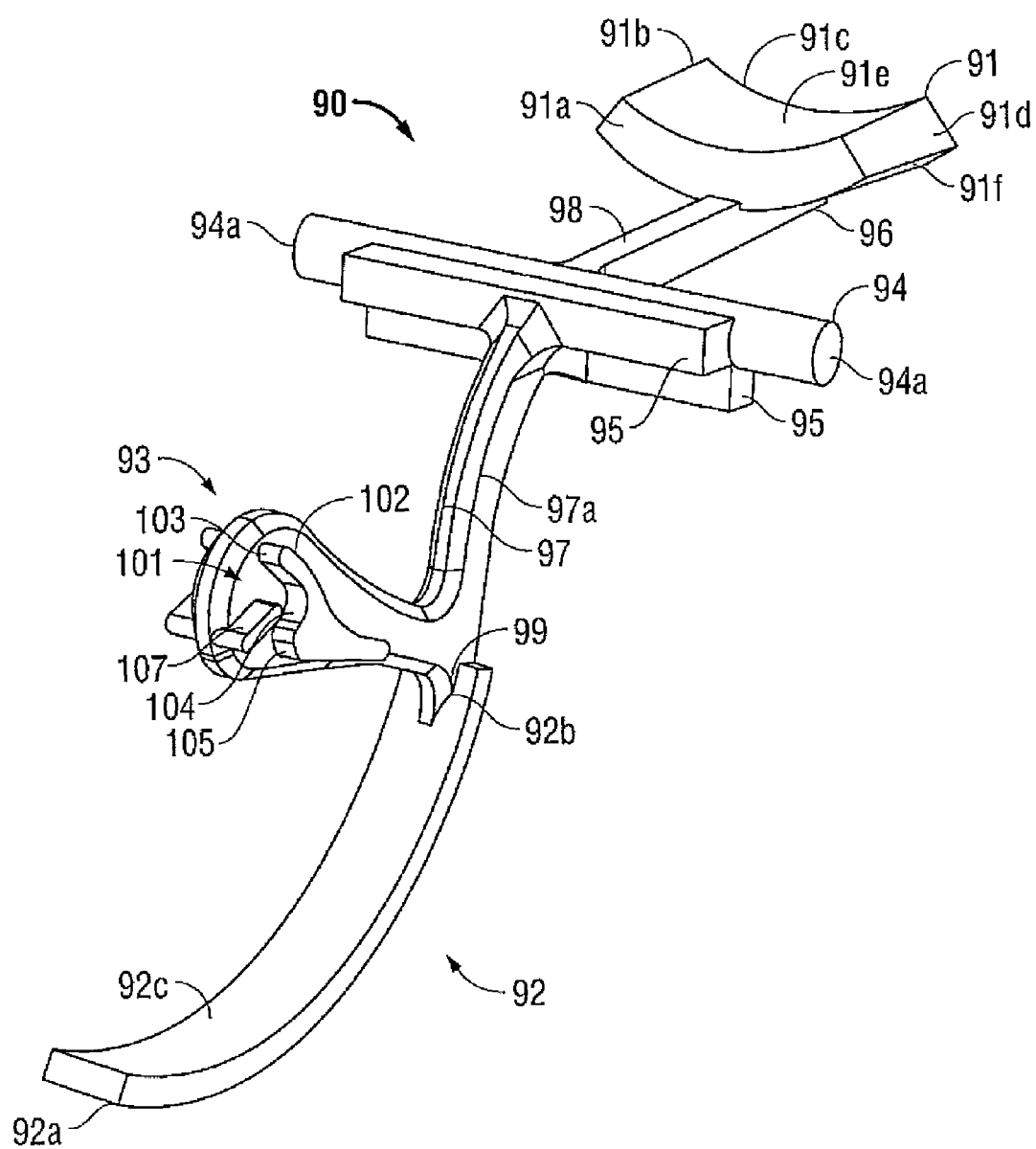
FIG. 3 is a left perspective view of the lock assembly depicted in FIGS. 2A-2D.

Pivot pin 94 is supported on the lock assembly 90 by two support beams 95 that are disposed at right angles with respect to each other (FIG. 3). Support beams 95 include arcuate distal edges that are contoured to cradle the pivot pin 94 therein. The contoured distal edges of the support beams 95 facilitate rotation of the pivot pin 48 in the relatively limited space within the housing 20.

With reference again to FIG. 3, lock assembly 90 is illustrated including a locking member 91, a beam spring 92 and a state changing feature 93.

Figure 2A:
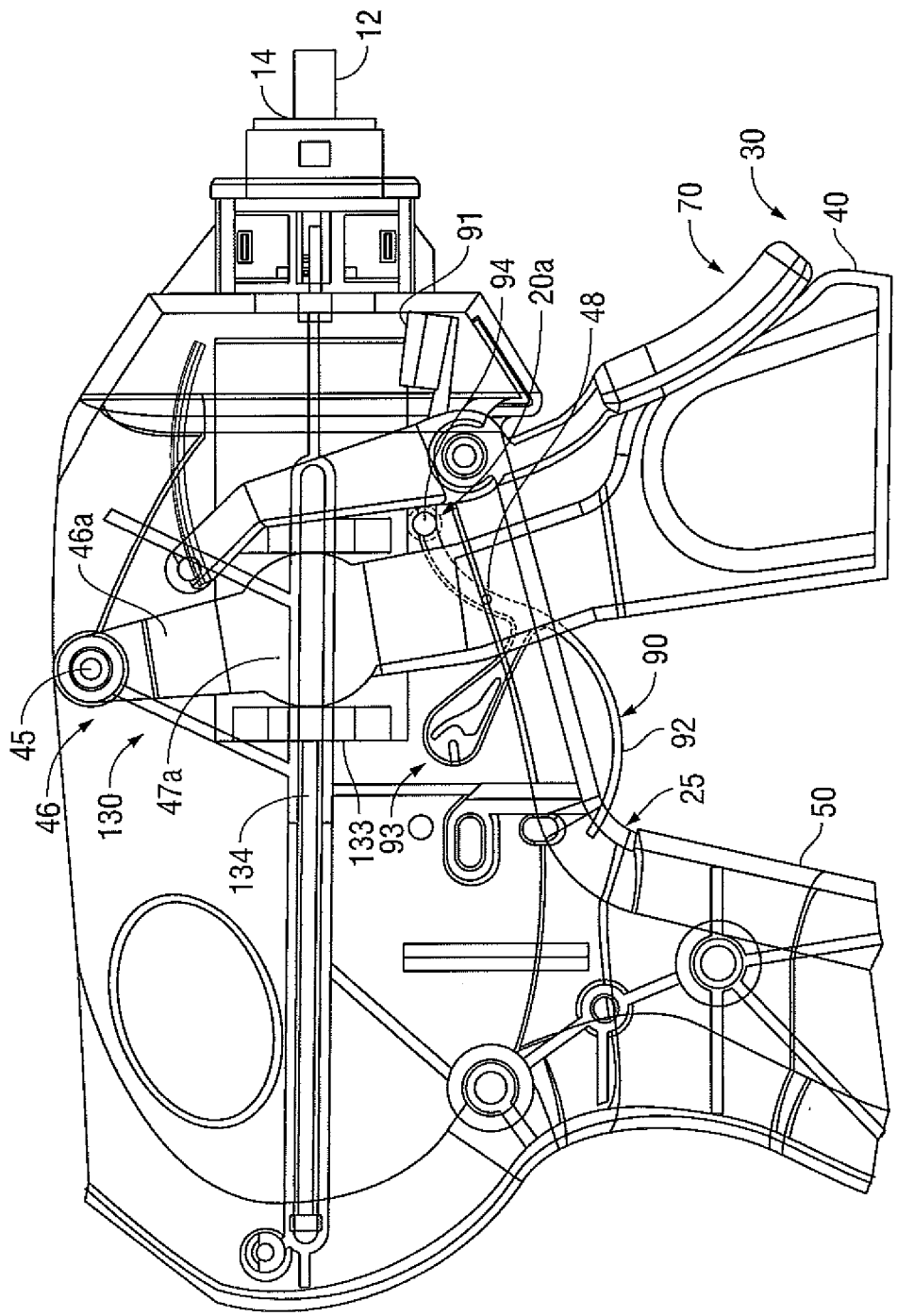
FIGS. 2A-2D are side, cut-away views of the bipolar forceps of FIG. 1A with the internal working components of the bipolar forceps exposed showing the handle assembly and the lock assembly in various positions.
Figure 2B:
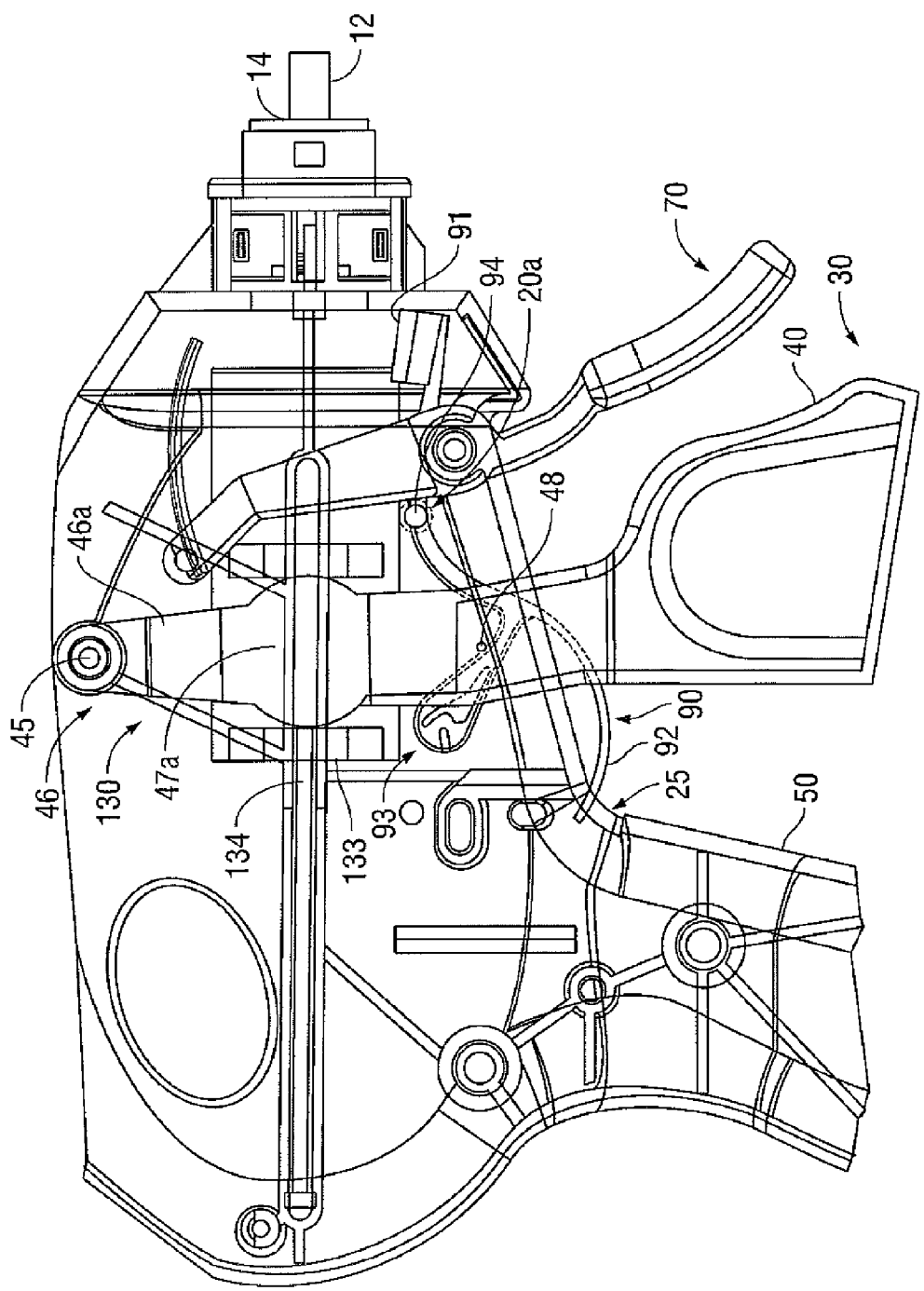
Figure 2C:
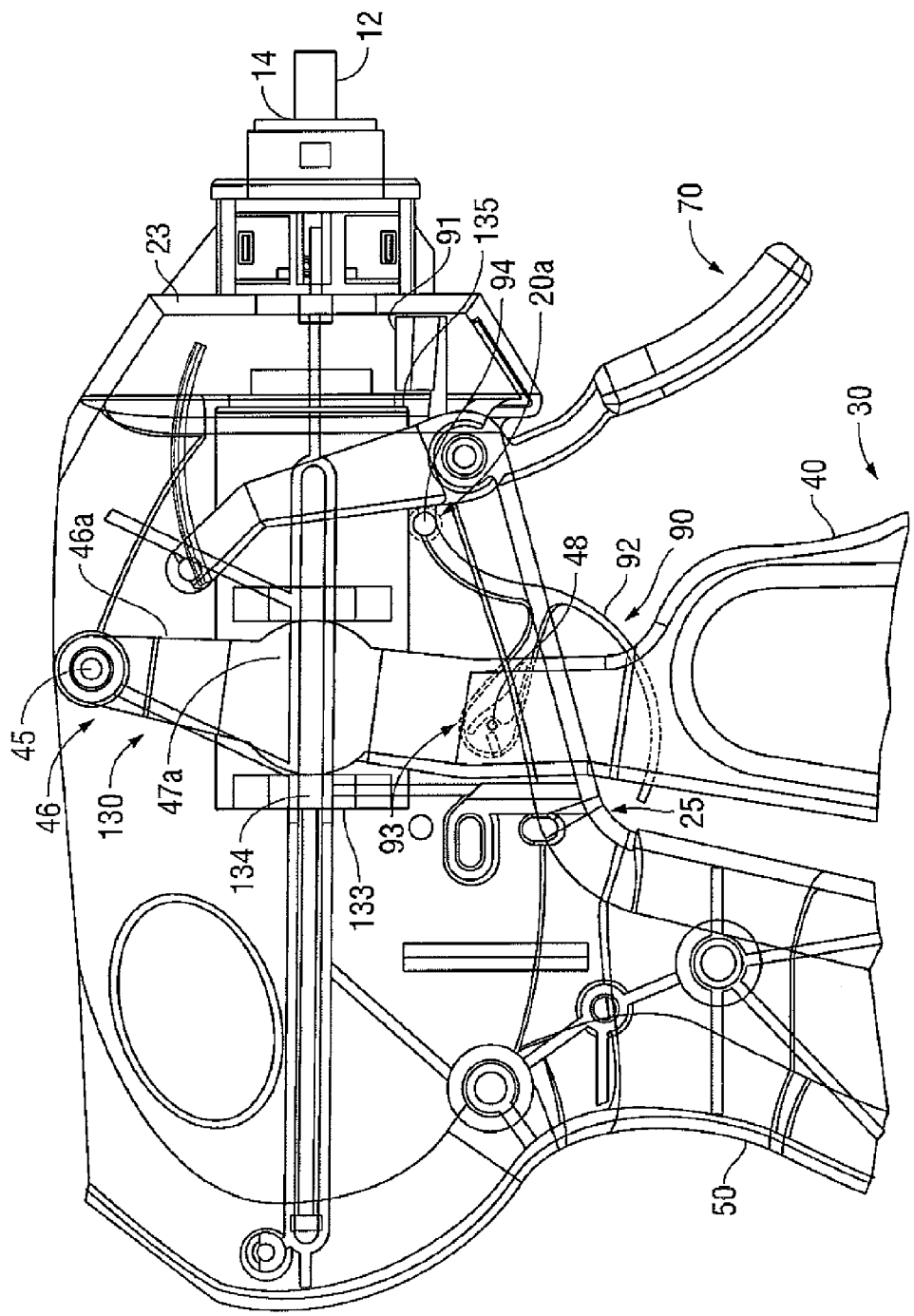

Locking member 91 is operably disposed at a distal end 96 of the lock assembly 90. Locking member 91 is configured to contact a distal end 135 of the spring cartridge 133 and a distal end 23 of the housing 20 when the movable handle 40 is moved proximally to the locked position, i.e., the locking member 91 is "wedged" or "sandwiched" between the distal end 135 of the spring cartridge 133 and the distal end 23 of the housing 20 (as best seen in FIG. 2C) thereby carrying the entire clamping force from the spring cartridge 133 in compression directly to the proximal end 14 of the shaft, thus, bypassing the handle flex. In the locked position, the jaw members 110 and 120 remain in the clamping position until a user moves the movable handle 40 proximally past the locked position through the release stroke, described in greater detail below.

Figure 4:
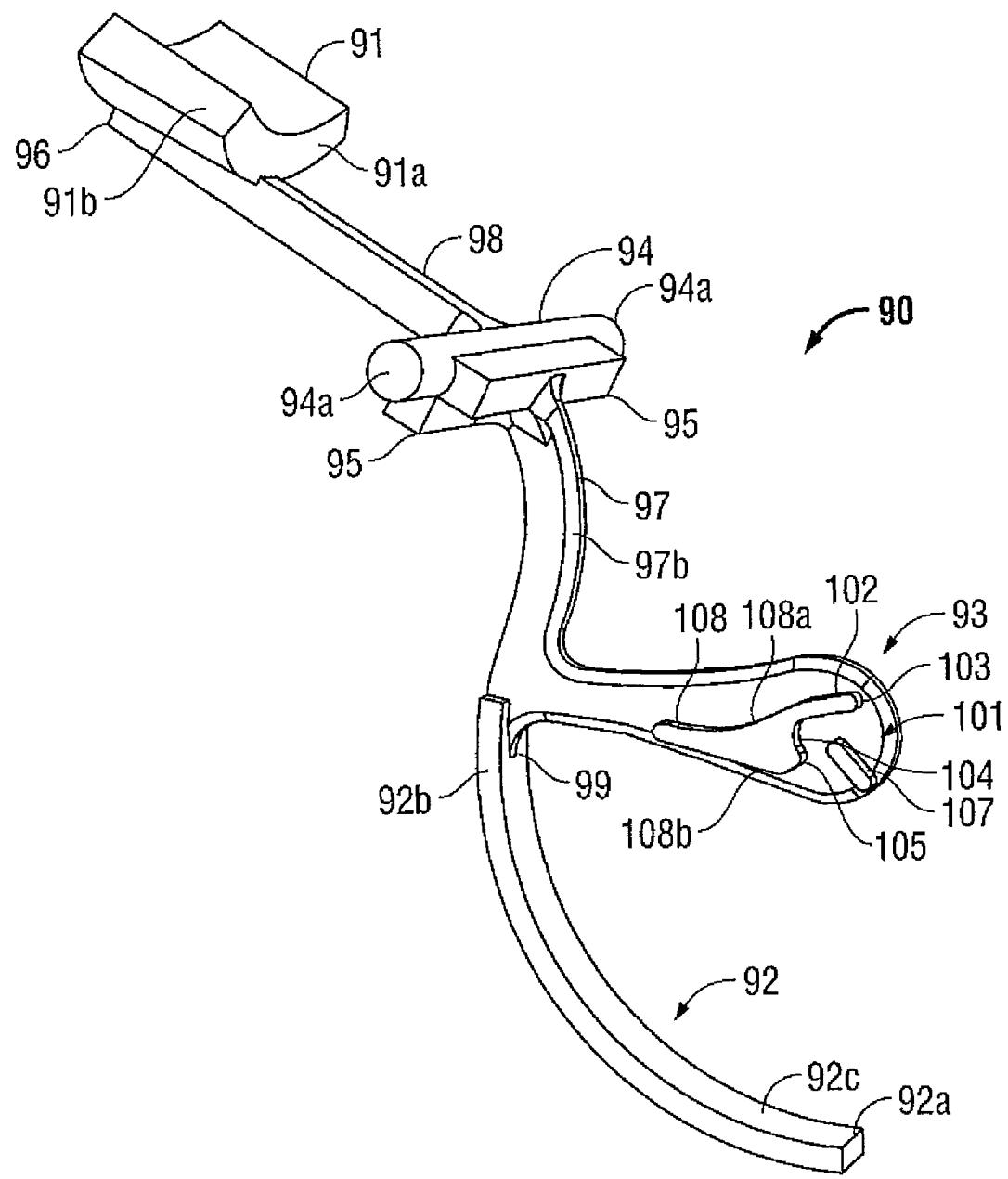
FIG. 4 is a right perspective view of the lock assembly.
Figure 5:
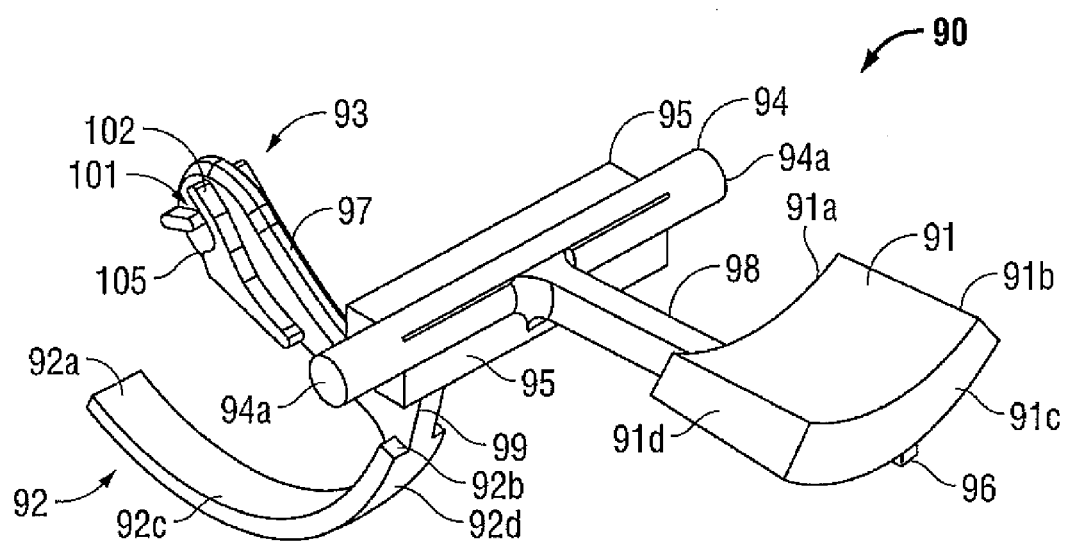
FIG. 5 is a rear perspective view of the lock assembly.
Figure 6:
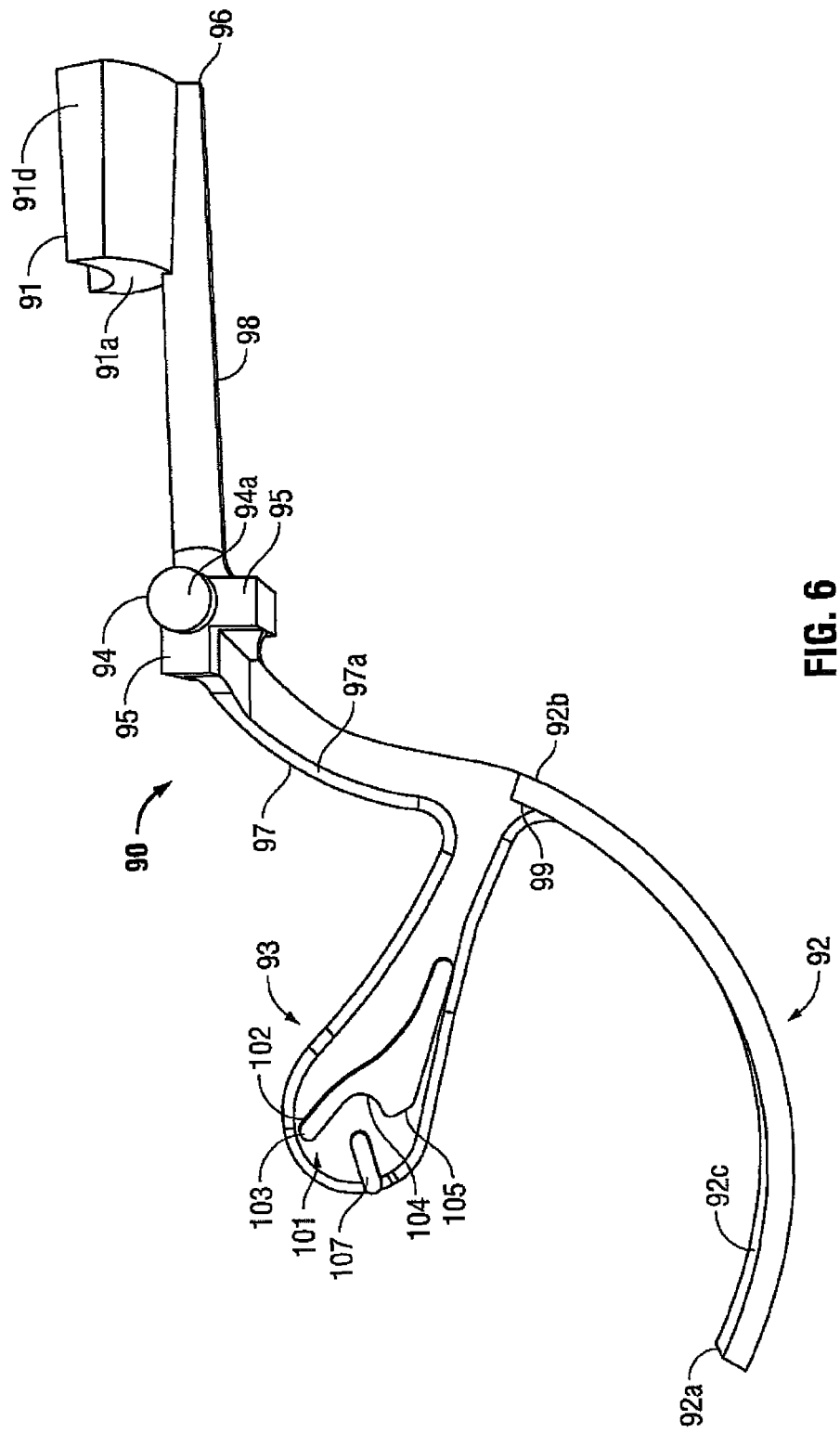
FIG. 6 is a left side view of the lock assembly.
Figure 7:
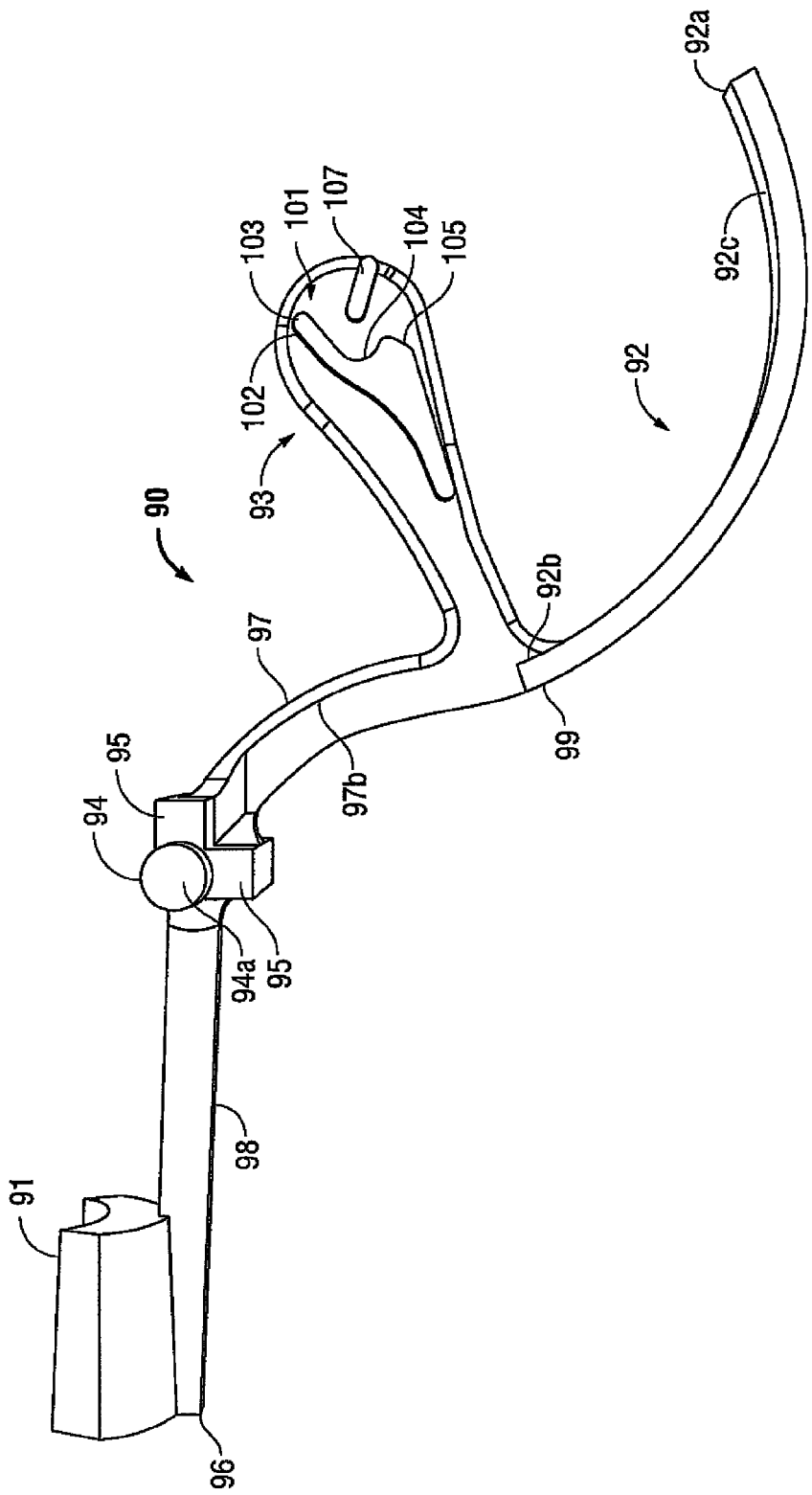
FIG. 7 is a right side view of the lock assembly.

Locking member 91 includes a generally arcuate or concave configuration having top and bottom portions 91e and 91f, respectively, and four sidewalls 91a-91d, see FIGS. 3-5. The arcuate or concave configuration of the locking member 91 follows the generally cylindrical contour of the distal end 135 of the spring cartridge 133. This arcuate or concave configuration of the locking member 91 is designed to evenly distribute (or concentrate) a load provided by the spring cartridge 133 against locking member 91, e.g., sidewall 91a. Evenly distributing or concentrating the load against the locking member 91 prevents or diminishes a top portion of the spring cartridge 133 from "pushing over" or "pivoting about" the locking member 91. Over time, this "pushing over" or "pivoting about" the locking member 91 may distort the spring and/or spring cartridge 133. Accordingly, the unique arcuate configuration of the locking member 91 increases the operative life expectancy of the spring, spring cartridge 133 and/or the forceps 10.

Locking member 91 is supported at the distal end 96 by a generally rectangular support beam 98 that extends from the pivot pin 94 adjacent the support beams 95 to the bottom portion 91f of the locking member 91, see FIGS. 3-5. The support beam 98 is configured such that one or more features, e.g., trigger assembly 70, associated with the forceps 10 are operable thereabout. More particularly, the support beam 98 is configured such that the trigger assembly 70 is pivotably movable therealong and between the pivot 94 and locking member 91, see FIGS. 2A-2D. Positioning the trigger assembly 70 in this manner facilitates pivoting of trigger assembly 70 in the relatively limited space within the housing 20. In embodiments, the support beam 98 may be configured to support or guide the trigger assembly 70. Moreover, support beam 98 also functions as a resilient member. More particularly, when state changing feature 93 is forced downward by pin 48, the locking member 91 is forced into contact with a bottom portion of the spring cartridge 133. The support beam 98 flexes until the spring cartridge 133 is fully proximal, at which point the force provided by the flexed support beam 98 drives the locking member 91 into a space between the distal end 135 of the spring cartridge 133 and an inside surface of distal end 23 of the housing 20. As a result thereof, all force of the spring cartridge is carried in compression by the locking member 91 and not through the sidewalls and fixed handle parts of the housing 20.

Referring back to FIG. 3, state changing feature 93 (feature 93) is operably disposed between the pivot pin 94 and the beam spring 92. Feature 93 may include any suitable configuration that is suitable for the intended purposes described herein. More particularly, feature 93 is configured to pivotally move the lock assembly 90 including the locking member 91 such that the locking member 91 is forced between the spring cartridge 133 and the distal end 23 of the housing 20. With this purpose in mind, feature 93 may include one or more cut-outs, protuberances, detents, intents, grooves, channels, railways, etc. that individually or collectively pivotally move the lock assembly 90. Moreover, to facilitate assembling the forceps 10, the feature 93 is configured to accommodate various configurations of pin 48 and/or movable handle 40, i.e. placement of the pin 48 on an interior left side of the movable handle 40 or the interior right side of the movable handle 40. As noted above, since pin 48 is described in terms of use on the interior right side of the movable handle 40, the operative components of the feature 93 that are configured for use with the pin 48 on the right interior side of the movable handle 40 are described hereinafter.

In the illustrated embodiment, a railway 97 extends along an outer periphery of the feature 93 from the support beams 95 of the pivot 94 to a proximal end 99 of the feature 93 adjacent the beam spring 92 (FIGS. 3, 4, 6 and 7). Railway 97 includes two generally slanted or beveled sidewalls of suitable proportion, see FIGS. 3 and 4, respectively. More particularly, railway 97 includes a right sidewall 97a and a left sidewall 97b. The slanted or beveled sidewalls 97a and 97b prevent the pin 48 from engaging or "catching on" the railway 97 as the lock assembly 90 moves distally to the open position. Moreover, and as described above with respect to support beam 98, railway 97 functions as a resilient member. More particularly, when state changing feature 93 is forced downward by pin 48, the locking member 91 is forced into contact with a bottom portion of the spring cartridge 133. The railway 97 flexes until the spring cartridge 133 is fully proximal, at which point the force provided by the flexed railway 97 drives the locking member 91 into a space between the distal end 135 of the spring cartridge 133 and an inside surface of distal end 23 of the housing.

Proximal end 101 is configured to selectively and releasably engage the pin 48 therein to thereby rotate the lock assembly 90 counterclockwise into the locked position, as best seen in FIG. 2C. To this end, the proximal end 101 is suitably proportioned and includes one or more suitable configurations. In the illustrated embodiment, proximal end 101 includes a generally "boot" like configuration having a generally arcuate proximal sidewall 102 defining a cul-de-sac 104 thereabout (FIGS. 3, 4, 6 and 7).

Cul-de-sac 104 includes a bottom portion 105 with a generally arcuate configuration that is configured to slidably engage the pin 48 when the movable handle 40 is moved proximally past the locked position and through the release stroke (FIG. 3). The arcuate configuration of the bottom portion 105 maintains the pin 48 within the confines of the cul-de-sac 104 and provides a smooth transition therefrom when the movable handle 40 is moved proximally past the locked position and through the release stroke.

Cul-de-sac 104 is proportioned to selectively and releasably engage or "cradle" the pin 48 when feature 93 moves upward against 48 during the proximal motion of the movable handle 40 (FIG. 2C). To this end, a generally elongated portion 107 is operably disposed adjacent the proximal portion 101 and is configured to arrest the upward motion of feature 93 against pin 48 and allow pin 48 into and out of the cul-de-sac 104 (FIGS. 3-7). More particularly, elongated portion 107 is configured to catch or trap itself on the pin 48 when the pin 48 is moved past a proximal end 103 (FIG. 3). That is, as the movable handle 40 and pin 48 moves distally into the locked position, the elongated portion 107 catches the pin 48 and prevents the lock assembly 90 from rotating counterclockwise out of the locked position.

A distal end 108 is configured to help rotate the lock assembly 90 counterclockwise as pin 48 moves to the top portion 103 of the proximal end 101. To this end, the distal end 108 includes a top portion 108a with a generally slanted, elongated configuration, see FIGS. 3-7. Likewise, a bottom portion 108b is configured to help guide the pin 48 along the railway 97a and back toward to the support beam 95.

Referring again to FIG. 3, the lock assembly 90 includes a beam spring 92. Beam spring 92 may include any suitable configuration. In the illustrated embodiment, the beam spring 92 includes a generally arcuate configuration having relatively flat proximal and distal faces 92c and 92d (FIGS. 3 and 5), respectively. Beam spring 92 includes proximal and distal ends 92a and 92b, respectively. Distal end 92b operably couples to the feature 93. Proximal end 92a is in operative communication with the housing 20. More particularly, proximal end 92a is movably disposed within a cavity 25 (of suitable proportion) of the housing 20 (FIGS. 2A and 2B). Proximal end 92a is configured to move out of communication with the cavity 25 when the movable handle 40 is moved to the locked position (FIG. 2C) and back into communication with the cavity 25 when the movable handle 40 is moved out of the locked position, see FIG. 2D, for example.

Beam spring 92 (in conjunction with the feature 93) is configured to rotate the locking member 91 about the pivot pin 94 in a clockwise direction. More particularly, as the pin 48 moves along the railway 97 (FIGS. 2A-2D) and into communication with the proximal end 101, the proximal end 92a of the beam spring 92 flexes against the internal frame of the housing 20, as best seen in FIGS. 2A and 2B. With the pin 48 positioned in the cul-de-sac 104, the proximal end 92a of the beam spring 92 is disposed within the movable handle 40.

In use, movable handle 40, initially, is positioned in a distal position (FIGS. 1A and 2A). In the distal position, the jaw members 110 and 120 are in the open position and the pin 48 is positioned along the railway 97 between the pivot pin 94 and locking member 91 that, at this time, is not disposed between the distal end 135 of the spring cartridge 133 and distal end 23 of the housing 20. That is, the spring cartridge 133 is biased against the internal frame of the housing 20. Moreover, the proximal end 92a of the spring beam 92 is positioned within the cavity 23.

Proximal movement of the moveable handle 40 moves the spring cartridge 133 proximally against the bias of the spring contained therein (FIG. 2B), which, in turn, moves the jaw members 110 and 120 toward one another and into the clamping position. Proximal movement of the movable handle 40 also moves the pin 48 proximally along the railway 97 and toward feature 93. As the pin 48 moves along the railway 97, the feature 93 causes the proximal end 92a of the beam spring 92 to flex against the internal frame of the housing 20 (FIG. 2B).

Moveable handle 40 is moved proximally to the locked position (FIG. 2C). In the locked position, the pin 48 is positioned within the cul-de-sac 104 of the feature 93 and the locking member 91 is positioned between the distal end 135 of the spring cartridge 133 and the distal end 25 of the housing 20. In the locked position, the spring cartridge 133 is prevented from moving distally toward the distal end 23 of the housing 20. Moreover, the jaw members 110 and 120 are maintained in the clamping position under the force provided by the spring contained in the cartridge 133 (FIGS. 1B and 2C). In the clamping position, the spring provides a closure force at the jaw members 110 and 120 for sealing tissue, e.g., in the range of about 3 kg/cm$^2$ to about 16 kg/cm$^2$. In the locked position, the unique configuration of the locking assembly 90 transfers the spring forces from the compressed spring to the internal frame of the housing 20 via the locking member 91. Thus, the entire spring force is carried in compression by the locking member 91 directly between the proximal end 14 of the shaft 12 and the distal end 135 of the spring cartridge 133. As can be appreciated, this reduces and/or greatly diminishes handle or lever "flex" that is typically associated with conventional forceps.

Figure 2D:
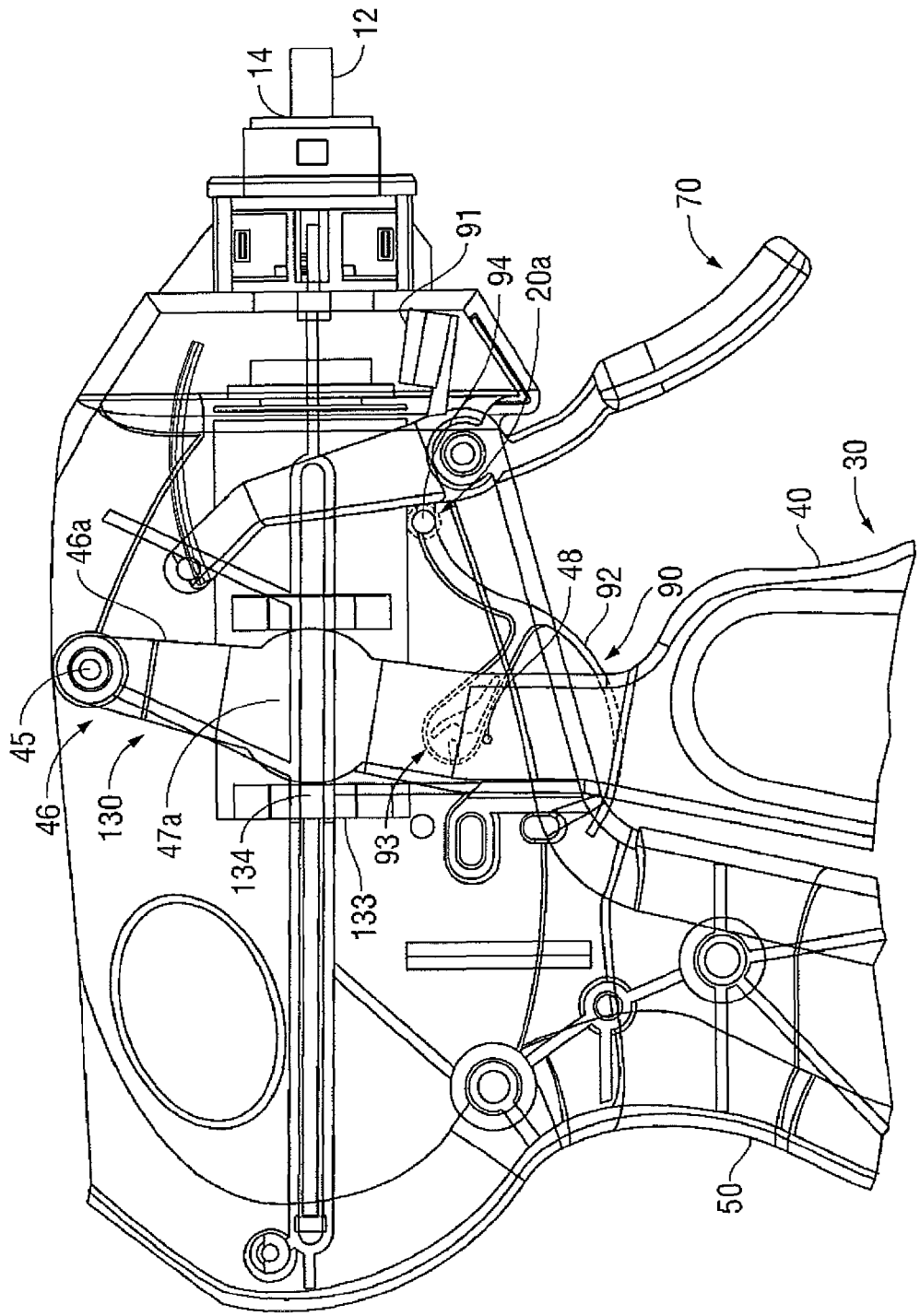

To unlock movable handle 40 from the locked position, movable handle 40 is moved proximally past the locked position through a release stroke, which, in turn, disengages the pin 48 from the cul-de-sac 104 (FIG. 2D). With the pin 48 disengaged from the cul-de-sac 104, the proximal end 92a of the spring beam 92 returns back to the cavity 25 where the proximal end 92a contacts and flexes against the internal frame of the housing 20, which, in turn, pivots the locking member 91 about the pivot 94 and moves the locking member 91 clockwise and out of engagement with the distal end 125 of the spring cartridge 133 and the distal end 23 of the housing 20 (FIG. 2D).

Once the pin 48 is disengaged from the cul-de-sac 104, the movable handle 40 returns to the distal position, the spring cartridge 133 biases against the distal end 23 of the housing 20, and each of the jaw members 110 and 120 returns to the open or neutral position.

From the foregoing and with reference to the various figure drawings, those skilled in the art will appreciate that certain modifications can also be made to the present disclosure without departing from the scope of the same. For example, it is contemplated that in certain instances one or more resilient members, e.g., compression spring (not shown), may be operably associated with or coupled to either the movable handle 40 and/or locking assembly 90.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:
1. An endoscopic forceps, comprising:
   a housing having a shaft that extends therefrom and defines a longitudinal axis therethrough;

a handle assembly including a movable handle movable relative to the housing, the movable handle including at least one mechanical interface disposed thereon;

an end effector assembly operatively connected to a distal end of the shaft and including a pair of first and second jaw members, at least one of the first and second jaw members movable relative to the other jaw member from an open position, wherein the first and second jaw members are disposed in spaced relation relative to one another, to a clamping position, wherein the first and second jaw members cooperate to grasp tissue therebetween;

a drive assembly including a having a bias operably associated therewith; and a lock assembly operably coupled to the housing about a pivot point disposed within the housing and in operative communication with the movable handle via the at least one mechanical interface disposed thereon, wherein the at least one mechanical interface moves along a top peripheral surface of the lock assembly within the housing when the movable handle is moved proximally causing the lock assembly to rotate about the pivot point for positioning a distal end of the lock assembly into engagement with at least a portion of the drive assembly such that the bias of the resilient member retains the first and second jaw members in the clamping position.

2. An endoscopic forceps according to claim 1, wherein the resilient member is a spring that is housed within a spring cartridge and the mechanical interface is a pin.

3. An endoscopic forceps according to claim 2, wherein a pivot pin is operably disposed on the lock assembly and is pivotably secured to the housing for rotating the lock assembly about the pivot point.

4. An endoscopic forceps according to claim 3, wherein the lock assembly is of unitary construction including a locking member, a beam spring and a state changing feature.

5. An endoscopic forceps according to claim 4, wherein the locking member is operably disposed at the distal end of the lock assembly and includes a generally arcuate configuration that is configured to contact a distal end of the spring cartridge and a distal end of the housing when the movable handle is moved proximally to a locked position such that the jaw members remain in the clamping position.

6. An endoscopic forceps according to claim 4, wherein the state changing feature is operably disposed between the locking member and the beam spring, the state changing feature configured to guide the at least one mechanical interface disposed on the movable handle along the lock assembly and into a cul-de-sac formed at a generally arcuate proximal end of the state changing feature.

7. An endoscopic forceps according to claim 5, wherein the beam spring is operably disposed at a proximal end of the lock assembly and selectively engageable with the housing, the beam spring configured to rotate the lock assembly in a clockwise direction such that the locking member is moved out of contact with the distal end of the spring cartridge and the distal end of the housing, and wherein the beam spring is configured to rotate the lock assembly in a counter-clockwise direction such that the locking member is moved into contact with the distal end of the spring cartridge and the distal end of the housing.

8. An endoscopic forceps according to claim 7, wherein the beam spring includes a generally arcuate configuration with a relatively flat profile to facilitate rotation of the lock assembly in the clockwise and counterclockwise direction.

9. An endoscopic forceps according to claim 3, wherein a portion of the lock assembly between the pivot pin and the locking member is configured to facilitate rotation of a trigger assembly operably associated with the forceps.

10. An electrosurgical forceps, comprising:

a housing having a shaft with a distal end thereof having an end effector assembly operatively connected thereto, the end effector including a pair of first and second jaw members pivotably coupled and movable relative to one another from an open position to a clamping position;

at least one movable handle movable relative to the housing and including at least one mechanical interface disposed thereon;

a drive assembly including a having a bias operably associated therewith; and a lock assembly operably coupled to the housing about a pivot point disposed within the housing and in operative communication with the movable handle via the at least one mechanical interface disposed thereon, wherein the at least one mechanical interface moves along a top peripheral surface of the lock assembly within the housing when the movable handle is moved proximally causing the lock assembly to rotate about the pivot point for positioning a distal end of the lock assembly into engagement with at least a portion of the drive assembly such that the bias of the resilient member retains the first and second jaw members in the clamping position.

11. An electrosurgical forceps according to claim 10, wherein the resilient member is a spring that is housed within a spring cartridge and the mechanical interface is a pin.

12. An electrosurgical forceps according to claim 11, wherein a pivot pin is operably disposed on the lock assembly and is pivotably secured to the housing for rotating the lock assembly about the pivot point.

13. An electrosurgical forceps according to claim 12, wherein the lock assembly is of unitary construction including a locking member, a beam spring and a state changing feature.

14. An electrosurgical forceps according to claim 13, wherein the locking member is operably disposed at the distal end of the lock assembly and includes a generally arcuate configuration that is configured to contact a distal end of the spring cartridge and a distal end of the housing when the movable handle is moved proximally to a locked position such that the jaw members remain in the clamping position.

15. An electrosurgical forceps according to claim 13, wherein the state changing feature is operably disposed between the locking member and the beam spring, the state changing feature configured to guide the at least one mechanical interface disposed on the movable handle along the lock assembly and into a cul-de-sac formed at a generally arcuate proximal end of the state changing feature.

16. An electrosurgical forceps according to claim 13, wherein the beam spring is operably disposed at a proximal end of the lock assembly and selectively engageable with the housing, the beam spring configured to rotate the lock assembly in a clockwise direction such that the locking member is respectively moved out of contact with the distal end of the spring cartridge and the distal end of the housing.

17. A lock assembly for use with a surgical instrument, comprising:

a state changing feature having a beam spring at one end thereof and a locking member at an opposite end thereof and a pivot pin configured to couple to an interior of a housing of a surgical instrument for coupling the lock assembly to the surgical instrument, the locking member including a generally arcuate configuration, the state changing feature including a generally arcuate proximal end, the beam spring selectively engageable with the housing of the surgical instrument and configured such that when a movable handle of the surgical instrument is moved proximally at least one mechanical interface disposed on a movable handle of the surgical instrument moves along a top peripheral surface of the lock assembly within the housing causing the lock assembly to rotate about the pivot pin in a clockwise and counter-clockwise direction for positioning a distal end of the lock assembly into and out of engagement with at least a portion of a drive assembly of the surgical instrument upon actuation of the lock assembly.

* * * * *